United States Patent [19]

Grisar et al.

[11] 4,111,556
[45] Sep. 5, 1978

[54] CONTROL SYSTEM FOR ALLOY TESTER

[75] Inventors: Ulrich Grisar; Wilhelm Berstermann, both of Georgsmarienhütte, Fed. Rep. of Germany

[73] Assignee: Klöckner-Werke AG, Duisburg, Fed. Rep. of Germany

[21] Appl. No.: 665,773

[22] Filed: Mar. 10, 1976

[30] Foreign Application Priority Data

Mar. 26, 1975 [DE] Fed. Rep. of Germany ....... 2513267

[51] Int. Cl.$^2$ .............................................. G01J 3/30
[52] U.S. Cl. ........................................ 356/86; 356/77; 356/81
[58] Field of Search ........................ 356/77, 79, 81, 86

[56] References Cited
PUBLICATIONS

"Direct-Reading Spectrometer for Ferrous Analysis" Carpenter et al., Josa vol. 37, #9, Sep. 1947, pp. 707–713.

*Primary Examiner*—Vincent P. McGraw
*Attorney, Agent, or Firm*—Michael J. Striker

[57] ABSTRACT

A workpiece is positioned in contact with a contact electrode and spaced by a gap from a counter electrode. A unipolar electrical pulse is passed across this gap during a first time period. Thereafter during a second time period the light from the spark drawn across the gap is diffracted into a spectrum having lines corresponding to a plurality of the components of the workpiece and these lines are transformed into respective electrical signals having intensities corresponding to the concentrations of the respective components in the workpiece. During this second period the pulse continues to pass across the gap and the signals are integrated. At the start of a third period the pulse is stopped and then the integrated signals are compared with respective reference signals and error signals are generated in the case of any variance between the two. Multivibrators with respective time constants and connected in a chain control the function of relay switches for establishing these operations in these time periods.

12 Claims, 4 Drawing Figures

Fig. 4

CONTROL SYSTEM FOR ALLOY TESTER

CROSS-REFERENCE TO RELATED APPLICATIONS

This application is related to our commonly assigned and jointly filed U.S. Pat. applications Ser. Nos. 665,770; 665,771; 665,772, and 665,774.

BACKGROUND OF THE INVENTION

The present invention relates to a method of and apparatus for testing a workpiece. More particularly this invention concerns a control system usable in combination with a spark-discharge apparatus and a spectrographic testing apparatus for determining the composition of an alloy.

It is known to test an alloy by positioning it on a contact electrode and spacing it by a gap from a counter electrode. A unipolar electrical pulse is then passed between the counter electrode and the workpiece to generate an arc or a spark of long duration. The light of this arc is diffracted into a spectrum having lines each corresponding to one of the components of the workpiece. Photocells arrayed to receive the respective lines form respective electrical signals having strengths corresponding to the intensities of the respective lines.

In our above-cited applications there is disclosed a system for integrating the several electrical signals corresponding to the lines for the various components of the workpiece and for thereafter comparing these integrated signals with reference values. The reference values may be derived from the signal corresponding to the basis metal or main component of an alloy so that when used in a steel plant, for example, the iron of the alloy is employed as a base value against which the others are compared. When any of the alloy components varies beyond a predetermined range from the desired composition an error signal is generated and the operator of the machine can appropriately alter the production process or eliminate the workpiece from the process.

A problem with such devices is that they are frequently extremely large and bulky and require carefully trained personnel to operate them. Thus a highly trained technician must stand ready at the apparatus in order to set it up to make the various test.

Another disadvantage of others of the known systems is that the counter electrode frequently oxidizes. Thus the first readings, at least, will often be falsified by the oxide layer on the counter electrode. Furthermore the workpieces themselves are almost invariably oxidized so that once again several readings must be taken before the results can be relied on.

Yet another disadvantage of the known testing machines is that calibrating them is a very complicated procedure which must usually be conducted by a trained metallurgist or the like. To do it the various controls of the machine must be set up in an altogether different manner as is the case when the machine is used simply for testing workpieces seriatim, and thereafter the machine must be programmed to make simple readings. Also inexact positioning of the counter electrode often gives an arc that generates inadequate light so that false readings occur during the inadequate time the device has to charge up. Another disadvantage is that the machine either cannot lock in once it makes a reading indicating that the workpiece is of an undesirable composition, or if it locks in a skilled technician again is required to restart the device.

SUMMARY OF THE INVENTION

It is therefore an object of the present invention to provide an improved testing method and apparatus.

Another object is the provision of an improved control system usable in combination with a spark-discharge apparatus and with a spectrographic testing apparatus.

Yet another object is to provide such an apparatus which overcomes the above-given disadvantages.

A further object is to provide an improved system for and method of testing the composition of a workpiece.

Another object is to provide an improved method and apparatus wherein the testing machine can be operated with virtually no training, can be calibrated easily, and can be reset after locking in on an error signal indicating an undesirable workpiece by even an untrained technician.

These objects are attained according to the present invention in a system for testing an alloy workpiece formed of a basis metal and a plurality of alloying elements. A power supply including a contact electrode adapted to engage the workpiece, a counter electrode adapted to be spaced by a gap from the workpiece, and an arc switch is provided for passing a unipolar electrical pulse across the gap to form a spark. A tester includes means for diffracting the light of the spark into a spectrum having lines corresponding to the basis metal and the alloying elements and for converting these lines into electrical signals having levels corresponding to the intensities of the respective lines. Means is provided in this tester including an integrate switch operable for integrating the electrical signals and an evaluate switch operable for reading the integrated signals and generating an error signal when any of these integrated signals varies from a predetermined range. The control circuit includes a frist timer connected to the arc switch for operating the same for a predetermined first period and thereby passing the pulse across the gap during the first period. A second timer in the control circuit is connected to the arc and integrate switches for operating these switches for a predetermined second period commencing at the end of the first period to continue passing the pulse and to integrate the electrical signals during the second period. A third timer in the control circuit is not connected to the arc switch but connected to the evaluate switch for operating the evaluate switch for a predetermined third period of time commencing at the end of the second period for terminating the spark and reading the integrated signals during the third period.

According to another feature of this invention the means for diffracting includes a receive switch which must be operated for conversion of the lines into electrical signals. The system further comprises a profilator connected only to the arc, receive, and evaluate switches for operating same in a profil mode. In profil mode the current from a photoelectric cell proportional to the intensity of a spectral line will be picked up for positioning of the spectral lines by means of shifting the primary slit of the spectrometer or for measuring this current for absolute determination of element-content in an alloy.

In accordance with the present invention once the workpiece is positioned on the contact electrode and spaced by a gap from the counter electrode the unipolar electrical pulse is passed across the gap during the first time period. Thereafter during the second time period the light of the spark formed by the pulse is diffracted into a spectrum having lines corresponding to the components of the workpiece, electrical signals are formed each having a signal level corresponding to the intensities of the respective lines, the signals are integrated, and the pulse continues to pass across the gap. Thereafter the pulse is stopped and during a third time period the integrated signals are compared with respective reference signals and an error signal is generated when any of the integrated signals varies from the respective reference signal by more than a predetermined amount.

In accordance with further features the improvement of the invention is usable in combination with a spark-discharge apparatus having a discharge switch operable to pass a unipolar pulse between the workpiece and an electrode, and with a spectrographic testing apparatus having means including a charging switch operable for charging a capacitor with an electrical signal corresponding to a spectral line of a diffraction spectrum produced from the spark created by the pulse. A first monostable multivibrator has an input and an output and a first NOR-gate has an output connected to the discharge switch for operating this switch and at least three inputs one of which is connected to the output of the first multivibrator. A second monostable multivibrator has an input connected to the other side of a first inverter whose one side is connected to the output of the first multivibrator and an output connected to another input of the first NOR-gate. A second NOR-gate has an input connected to the output of the second multivibrator and an output connected to the charging switch.

According to further features of this invention the testing apparatus also has an integrating circuit for reading the capacitor into an evaluating circuit and the control circuit further comprises a third NOR-gate having at least one input connected to the output of the second multivibrator and an output connected to the integrating switch. A second inverter has one side connected to the output of the second multivibrator in an arrangement wherein the testing apparatus has an evaluating switch operable for measuring the electrical energy stored in the capacitor. A third multivibrator has an input connected to the other side of the second inverter and an output connected to another input of the third NOR-gate and a fourth NOR-gate has at least one input connected to the output of the third multivibrator and an output connected to the evaluating switch to operate same.

The discharge apparatus according to this invention has a start switch operable to fire the pulse across the gap and the testing apparatus has an output and means for forming at this output an error signal when a workpiece being tested has a composition varying from a predetermined reference composition. In this arrangement the control circuit further comprises a start switch linked to the start switch of the discharge apparatus, a third inverter having one side connected to the start switch of the circuit, an AND-gate having one input connected to the other side of the third inverter and an output connected to the input of the first multivibrator, and a fourth inverter having one side connected to receive the error signal and another side connected to the other input of the AND-gate. In this arrangement the third NOR-gate has another input connected to said one side of said fourth inverter. It is also possible in this arrangement to provide the second multivibrator with a reset connection connected through a diode for means in a testing apparatus for generating a voltage proportional to the charge in the capacitor. This voltage is fed through the diode to the second multivibrator to reset this multivibrator when the charge in the capacitor attains a predetermined level.

In accordance with the present invention the testing apparatus need merely be started. It will then automatically draw an arc for a short period of time between the counter electrode and the workpiece and burn off any impurities on either of these elements. Thereafter the tester is switched in and the signals corresponding to the spectral lines of the components of the workpiece of interest are integrated during a second predetermined period. Thereafter during a third period the integrated signals are evaluated and, if the workpiece varies from the desired composition, an error signal is generated. This entire process takes place automatically once the start switch is operated. If the workpiece is not properly grounded to the contact electrode the safety circuit in the discharge apparatus will prevent an arc from being drawn in order to eliminate a shock hazard.

In accordance with this invention the device can be operated in profil mode by throwing a profil switch on the controller. Operation of this profil switch locks in the arc, receive and evaluate switches while leaving the integrate switch out of the circuit. For profiling the primary slit can be shifted until the reading of the voltmeter 240 signals maximum intensity. In this mode the voltmeter reading is proportional to the current of the photoelectric cells connected to it and therefore to the absolute concentration of the corresponding element.

According to yet another feature of this invention the time constant of the second multivibrator which controls the integrating cycle can be greatly increased. This multivibrator is reset only when a predetermined charge level has been attained by the tester. In situations where the arc is not likely to be bright enough always to produce a readable output, the device automatically lengthens the integrate period until sufficient light has been generated to obtain meaningful results.

In accordance with yet another feature of this invention the error signal is fed into the control system through an inverter and through an AND-gate to the first multivibrator. The start switch is also connected through an inverter and this AND-gate to the first multivibrator. Furthermore the error signal is also fed directly to the third and fourth NOR-gates controlling the integrate and evaluate relays so that in a situation where an error signal is generated, as where an alloy of undesirable composition is being tested, the device will not automatically recycle, but will continue to read-out the composition of the undesirable workpiece and will lock out the start switch so that the arrangement must be manually reset in order to allow another reading to be taken. This feature prevents the results of a test from being ignored. The reset button of the controller is also linked to the resets for the testing device so that a single switch can put the entire arrangment back into the starting position.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
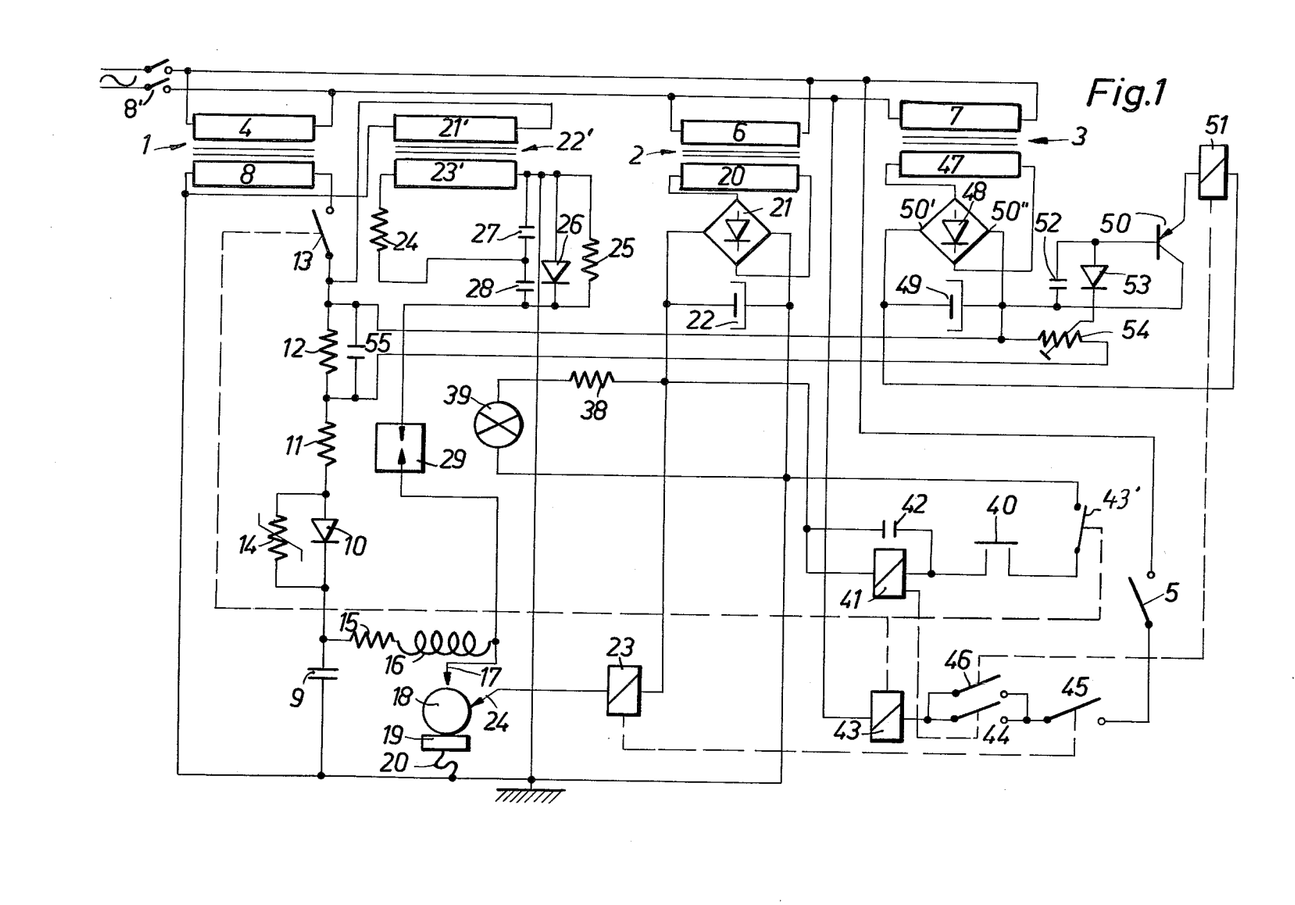
FIG. 1 is a schematic view of the proper supply for the testing system in accordance with the present invention.

As shown in FIG. 1, three transformers 1, 2 and 3 have their primary windings 4, 6 and 7 connected in parallel to line via a double-pole single-throw on-off switch 8'. The high-voltage secondary 8 of the transformer 1 is connected to a first loop in which is provided a condenser 9, a diode 10, a pair of series-connected resistors 11 and 12, and a normally open switch 13. Connected in parallel across the diode 10 is a varistor 14.

Connected in parallel across the condenser 9 is, in series a resistor 15, a coil 16, an electrode 17, a workpiece 18, another electrode 19, and a grounding cable 20. The electrode 17 is spaced by a gap from the workpiece 18 which itself lies in good electrical contact on the base or contact electrode 19. The coil 16 may be wound using resistance wire in order to eliminate the resistor 15. It should be clear that, so long as switch 13 is closed, a unipolar pulse will be fired across the gap between the electrode 17 and the workpiece 18.

Another transformer 22' is connected across the secondary 8 of the transformer 1 so that its primary 21' is only energized when the switch 13 is closed. The secondary 23' of this transformer 22' is connected to a voltage-doubling circuit comprising, in parallel, a resistor 25, a diode 26, and a pair of series-connected capacitors 27 and 28 betweeen which is connected a resistor 25 connected to one side of the secondary 23'. The other side of the secondary 23' is grounded. The high-voltage output from this circuit 25–28 is fed to an auxiliary spark gap 29 connected to the electrode 17. Thus closing of the switch 13 will cause a high voltage unipolar pulse to pass between the electrode 17 and the workpiece 18, assuming that the workpiece 18 is in good electrical contact with the base 19.

The secondary 20 of the transformer 2 is connected to a full-wave rectifier bridge 21 across which is connected a smoothing capacitor 22. One side of this full-wave rectifier 21 is connected to one side of a relay coil 23 whose other side is connected to a test terminal 24 engageable with the workpiece 18. The other side of the full-wave rectifier is connected to ground. In addition there is connected across this low-voltage power supply a mercury-vapor lamp 39 in series with a resistor 38 for preionizing the auxiliary gap 29. The terminal 24 must be in good electrical contact with the workpiece 18 which in turn must be in good electrical contact with the electrode 19 in order for this low-voltage loop to be closed and for current to pass through the coil 23.

Also connected across the full-wave rectifier 21 of the low-voltage power source is a third loop constituting a momentary-contact push-button switch 40 connected in series between a normally closed switch 43' and a relay coil 41. A condenser 42 is connected across this coil 41 and serves to maintain electrical energization of this coil 41 for a limited period of time after either of the switches 40 or 43' is opened.

Connected across the line is also a relay coil 43 in series with two normally-open switches 44 and 45. The switch 44 is operated by the relay coil 41 and the switch 45 by the relay coil 23. At the same time the coil 43 operates the normally closed switch 43' and the normally open switch 13. Another normally open switch 46 is also connected across the switch 44. A time-controlled switch 5 which is connected to a control circuit is also connected in series with the coil 43 so that this coil 43 can only be electrically energized when the switches 5 and 45 are closed as well as one of the switches 44 and 46.

The transformer 3 has a secondary winding 47 connected to a bridge circuit 48 having a pair of outputs 50' and 50" across which is connected a smoothing factor 49. A transistor 50 has its collector connected to the terminal 50" and its emitter connected through a load constituted by a relay coil 51 to the terminal 50'. The base of this transistor 50 is connected via a capacitor 52 to the terminal 50" and through a diode 53 to the wiper of a potentiometer 54 connected across the resistor 12 of the first loop. A capacitor 55 is also connected across the resistor 12 to smooth out the voltage changes thereacross. When current flows through the resistor 12 it is detected by the transistor 50 which actuates the coil 51 that operates and closes the switch 46.

The device described above functions as follows:

With the switch 8' closed and none of the other manually operable switches operated the only coil that can be electrically energized is the relay coil 23. This can only occur when the terminal 24 is in good electrical contact with the workpiece 18 and this workpiece 18 is in turn in good electrical contact with the base electrode 19. Assuming such good contact between the terminal 24 and the workpiece 18 and between the workpiece 18 and the electrode 19 current will flow through the coil 23 to close normally open switch 45 only.

In order to fire a pulse across the gap between the electrode 17 and the workpiece 18 the switch 40 is operated. The switch 40 is connected to the timer that operates the switch 5 so that switches 40 and 5 are closed simultaneously, with switch 40 opening again as soon as it is released by the finger of the operator but switch 5 only opening after a predetermined length of time. Momentary closing of the switch 40 with the relay contact 43' closed energizes the coil 41 and charges the capacitor 42. Energization of this coil 41 will close the contacts 44 in series with the contacts 45 and, since switch 5 remains closed for a predetermined amount of time after closing of the switch 40, this will allow energization of the coil 43 to open contacts 43' and close contacts 13.

As soon as contacts 13 are closed the first loop and the primary 21' of the transformer 22' are energized and a high-voltage pulse is fired across the gap between the electrode 17 and the workpiece 18. The light emitted by this spark can be spectrographically analyzed as described below.

Even though energization of the coil 43 will open contacts 43', it will not cause immediate open-circuiting for the coil 43 by opening the switch 44. First of all the condenser 42 across the coil 41 will discharge when the switch 43' or the switch 40 is open so that the relay coil 41 will remain closed for a short period of time after it is open-circuited. In addition the energization of coil 43 fires a spark across the gap 17 and 18 and causes a voltage drop across the resistor 12. This voltage drop is detected by the transistor 50 which then energizes the relay coil 51 and closes the switch 46 in parallel to the switch 44. The circuit is adjusted so that the switch 46 will close shortly before the switch 44 opens to maintain the relay coil 43 energized continuously. The pulsing then continues until the switch 5 is automatically opened, to deenergize the coil 43 which in turn will open the switch contacts 13 and shut down the whole system, except for the safety loop including the coil 23.

The normally closed contacts 43' are provided in order to insure that the pulsing will follow a predetermined program once the switch 40 is actuated. Actuating of the switch 40 after the start of a pulse and before the end thereof will have no effect as the contacts 43' will be open.

With the system according to the present invention it is impossible to fire the unipolar pulse between the electrode 17 and the workpiece 18 unless this workpiece 18 is in good electrical contact with the base electrode 19. Thus shock hazard for the operator of the machine is almost completely eliminated, and it is possible to make the machine portable without a loss in safety. Furthermore the heavy-duty relay 43 which must operate the heavy-current switch 13 may operate off line voltage directly, whereas the light-duty switching relay 41 can operate off a much lower voltage and, therefore, allow the mounting of the switch 40 at a remote location from the device. The apparatus according to this invention is, therefore, almost fool-proof and very safe.

Figure 2:
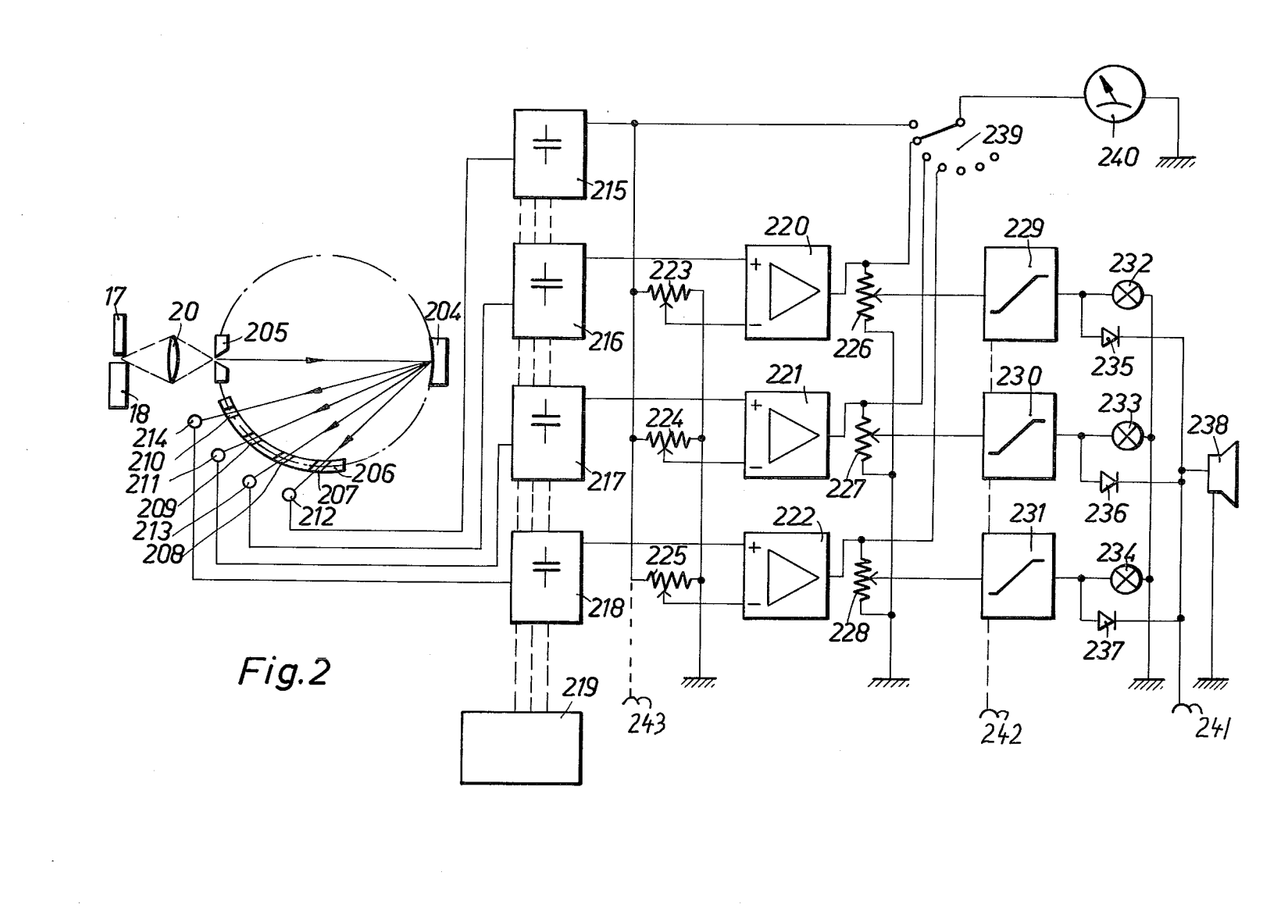
FIG. 2 is a schematic diagram of the tester in accordance with the present invention.

The arrangement shown in FIG. 2 is employed for testing the composition of an alloy workpiece 18 which is juxtaposed with an electrode 17 connected to one side of the power supply described above whose other side is connected to this workpiece 18.

A unipolar electrical spark is therefore fired between the two elements 17 and 18. A lens 20 picks up the light from this spark and focuses it through the primary slit 205 of a Rowland-type diffraction spectrometer having a concave grating 204 and four slots 207–210 on the Rowland-circle 206.

These slots 207–210 each, therefore, pass a respective spectrum line to a respective photocell 212, 213, 211 and 214. The angular spacing of the slots 207–210 on the surface 206 determines which components of the workpiece sample 18 are to be analyzed, and each of the photocells 211–214 will therefore produce an output signal whose electrical level will be proportional to the intensity of the spectrum falling on it. In the illustrated system the slot 207 is aligned to receive the spectral line for iron, the slot 208 the spectral line for chromium, the slot 209 the spectral line for copper, and the slot 210 the spectral line for molybdenum.

Each of these photocells 211, 212, 213 and 214 is connected to a respective integrator 217, 215, 216 and 218. These integrators 215–218, which will be described in more detail below, are operated by a clock-type controller 219. Each of these integrators 215–218 therefore produce an integrated electrical signal having a voltage level proportional to the intensity of the respective spectrum line.

The outputs of the three alloying-element integrators 216, 217, and 218 are each fed to one uninverted input of a differential amplifier 220, 221 and 222, respectively. The output signal of the iron or basis-metal integrator 215 is fed to one side of each of three potentiometers 223, 224 and 225 whose other sides are grounded and each of which has a wiper connected to the inverted input of a respective one of the differential amplifiers 220, 221 and 222. These differential amplifiers 220, 221 and 222 therefore produce respective output signals corresponding to the difference between their respective inputs, these output signals each being applied across a respective potentiometer 226, 227 and 228 whose other side grounded.

A selector switch 239 can connect a voltmeter 240 to the outputs of each of the differential amplifiers 220, 221 and 222 as well as to the output of the basis-metal integrator 215. The wipers of the potentiometers 226, 227 and 228 are connected to respective threshold circuits 229, 230 and 231 in turn connected to respective visual signals 232, 233 and 234 which illuminate when the level of the signal detected by the respective threshold circuit exceeds a predetermined threshold level. In addition the outputs of these threshold circuits 229, 230 and 231 are connected via diodes 235, 236 and 237 to an acoustic signaller 238, here a speaker.

An outlet jack 241 is provided with the speaker 238 to allow a remote alarm to be connected, and connections 242 are provided to the threshold devices 229–231.

The system according to the present invention functions as follows:

Assuming that the device is to be set up to act only if a sample has a composition of say, 80% iron, 5% chromium, 10% copper, and 5% molybdenum, a test sample 18 having the desired composition is placed under the electrode 17 and a spark is passed between this electrode 17 and the workpiece 18. The resultant signals on the outputs of the integrators 215, 216, 217 and 218 are then weighed against the output of integrator 215 by varying the respective potentiometers 223, 224 or 225 one after the other with the voltmeter 240 connected to the output of the respective differential amplifier 220, 221 or 222 so as to reduce this output to zero. The ranges can then be determined by setting the potentiometers 226, 227 and 228 to establish just how much the output signal of the differential amplifiers can vary before the respective threshold device will trigger the respective signal.

Although discussion has been made above to a mainly iron alloy, it lies within the scope of this invention to test any other type of alloy, the positioning of the slots 207–210 determining just what components of the test sample are being analyzed. It is clear that the number of slots and therewith the number of elements to be tested is generally not limited.

Figure 3:
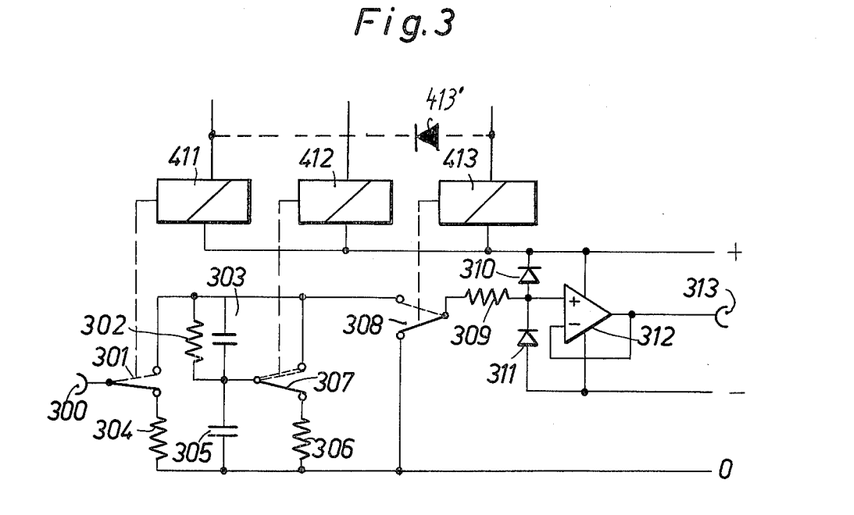
FIG. 3 is a detail view of an element of the circuit of FIG. 2.

FIG. 3 shows an integrator having an input 300 from the respective photocell. A relay 411 when not activated by the controller 219 connects the input 300 with its pole 301 through a resistor 304 to ground. When the relay 411 is switched on, however, its pole 301 connects the photocell input 300 to a resistor 302 and a capacitor 303 in parallel with each other and connected on their other sides to a pole 307 of a relay 412 and through a capacitor 305 to ground. Absent activation of the relay 412 the pole 307 connects a resistor 306 across the capacitor 305, but the electrical actuation of this relay 412 causes the pole 307 to shunt across the resistor 302 and capacitor 303, thereby connecting the capacitor 305 to one terminal of a relay 413 having a pole 308. The pole 308 normally connects one input of a FET operational amplifier 312 through the resistor 309 to ground. Then actuated the relay 413, however, connects the input of this operational amplifier 312 as shown in dashed line. Overload-protecting diodes 310 and 311 are connected across the operational amplifier 312 which has an output 313 that is adapted to be connected to a differential amplifier as described above. The charge of the capacitor 305 appears at the output 313 when the poles 307 and 308 are in the dashed-line position. During the integration the poles 301 and 307 lie in their dashed-line positions. The integrator 215 for reference has an additional diode 413', as shown by dashed lines, which actuates relay 413 together with relay 411 actuating the voltage of capacitor 305 appearing at the output 243.

It is possible to use this device right in a production line to ascertain the composition of workpieces passing along the line. Furthermore, an automatic sorter connected to the output 241 can be employed automatically to shunt aside any workpiece which does not have a composition within the desired range.

Figure 4:
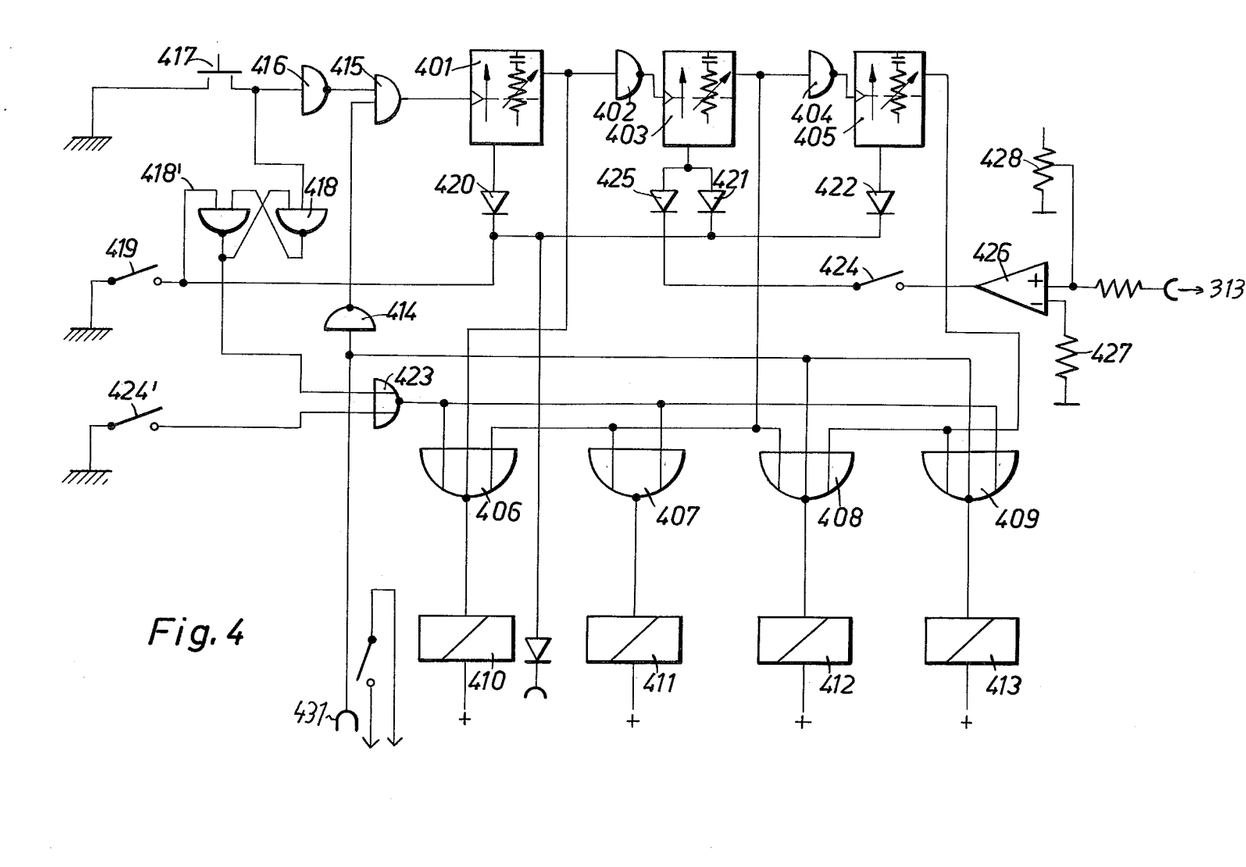
FIG. 4 is a schematic view of the control circuit for the system according to the present invention.

FIG. 4 shows the control circuit for the power supply of FIG. 1 and the analyzer of FIGS. 2 and 3, some of the parts of these subsystems being shown in FIG. 4.

A first multivibrator 401 is connected through an inverter 402 to a second multivibrator 403 whose output in turn is connected through another inverter 404 to the input of a third multivibrator 405. These multivibrators are of the monostable type and have time constants which may be varied. The output of the first multivibrator 401 is connected to a three-input NOR-gate 406 whose output is connected to the arc relay 410. The output of the second or integrate multivibrator 403 is connected to another input of the NOR-gate 406, to one of two inputs of a NOR-gate 407 operating the receive relay 411, and to one of the three inputs of a NOR-gate 408 whose output is connected to the integrate relay 412. The output of the third or read multivibrator is connected to another input of the NOR-gate 408 and to one of the three inputs of a NOR-gate 409 whose output is connected to the evaluate or read relay 413. The relay 410 operates the timer switch 5 shown in FIG. 1.

An input 431 receives an error signal from the output 241 of the analyzer of FIG. 2 and feeds it through an inverter 414 to one input of an AND-gate 415 whose output is connected to the input of the arc multivibrator 401. In addition this error-signal input 431 is connected to an input of the NOR-gates for the integrate relay 412 and for the evaluate relay 413. The other input of the AND-gate 415 is connected through an inverter 416 to a momentary-contact start switch 417 that is ganged with the start switch 40 shown in FIG. 1.

Thus when an error signal appears at the output of any of the threshold devices 229–231 (FIG. 2) it will be fed to the NOR-gates 408 and 409 to hold the relays 412 and 413 closed, thereby locking the reading in the analyzer. This error signal will also be fed through the inverter 414 to the AND-gate 415 to lock the control circuit and prevent actuation of the start switch 417 from being effective to start cycling of the multivibrator 401 as will be described below. The input of the inverter 416 which is connected to the grounded start switch 417 is also connected to an input of one of two NAND-gates 418 and 418' forming a flip-flop. The inverted output of the gate 418 is connected to the input of the gate 418' and the inverted output of the gate 418' is connected to one of the inputs of the gate 418. The other input of the gate 418' is connectable to ground through a reset switch 419 which may also ground any of three diodes 420, 421 and 422 connected to the reset terminals of the arc, integrate, and read multivibrators 401, 403 and 405.

The output of the NAND-gate 418' is connected also to one input of a NOR-gate 423 whose output is fed to one input of the NOR-gate 406, the NOR-gate 407 and the NOR-gate 409. The other input of this gate 423 is connectable to ground via a profil switch 424', which serves for setting the profil of spectral lines and for measuring the current of the photoelectric cells for each element.

The reset connection of the integrate multivibrator 403 is connected through a diode 425 to a switch 424 itself connected to the output of a differential amplifier 425 whose inverted input is connected through a resistor 427 to a reference voltage source while the other not-inverted input is connected through variable resistor 428 to the voltage source to receive a variable positive voltage and through a resistor 429 to the output of a reference signal from the analyzer of FIG. 2. Here the resistor 429 is connected to the pole 313 of the integrator 215 via contact 243.

The device operates as follows:

So long as the switches 419 and 424 are open and switch 424' is closed and there is no error signal applied to the input of the inverter 414, the start switch 417 and the start switch 40 are simultaneously momentarily actuated to start the device. The switch 417 will feed a "0" pulse to the input of the inverter 416 so that a "1" pulse will be fed from its output to the input of the AND-gate 415. Since the input of the inverter 414 is not live, therefore carrying a "0", its output will also be at "1" so that two "1" signals will be fed into the AND-gate 415 which will produce a "1" at its output that will be fed to the monostable multivibrator 401 and cause the output of this multivibrator to switch from "0" to "1" for a period of time dependent on the time constant of this multivibrator 401. As soon as the output of the multivibrator 401 becomes "1" the inverted output of the NOR-gate 406 will become "0" or ground in this case and the relay 410 will be closed.

After this arcing or prearcing period the multivibrator 401 will automatically go from its metastable condition in which its output is "1" to its stable condition in which its output is "0." Such a change in state will be fed in reverse to the input of the integrate multivibrator 403, that is as a change from "0" to "1," causing this multivibrator 403 to move from the stable condition to the metastable condition where its output is "1." Such change in state is fed to the three NOR-gates 406, 407 and 408. Thus the arcing relay is maintained locked and the switch 5 closed. At the same time the receiving relay 411 is closed to feed the input 300 (FIG. 3) into the integrator and the relay 412 is also closed to apply the input to the integrating capacitor 305. Once again this condition is maintained for a period determined by the time constant of the multivibrator 403.

Again reversion of the multivibrator 403 from its metastable state to its stable state will cause the read multivibrator 405 to be switched from its stable state to its metastable state. The output of this multivibrator 405 is connected only to the NOR-gates 408 and 409. Thus in the read period the relay 412 will be closed and the relay 413 will be closed to feed the charge in the capacitor 305 to the input of the differential amplifier 312. During this read period the pole 301 moves back to the solid-line position of FIG. 3 and the arc between the counter electrode 17 and workpiece 18 of FIG. 2 is extinguished by opening of the switch 5 of FIG. 1.

If the workpiece being tested has a composition within the desired range no error signal will be fed into the input 431. After the period determined by the time constant of the multivibrator 405 this element will revert to its stable condition and the device will be ready for another test cycle, all of the relays 410–413 being deenergized.

If the workpiece, however, does not correspond to the desired composition an error signal will be fed by the threshold devices 229, 230 and 231 through their output 241 to the input 431. This error signal will be fed to the two NOR-gates 408 and 409 which will, therefore, hold the relays 412 and 413 closed regardless of the states of any of the multivibrators 401, 403 and 405. In addition this input at 431, which is a "1" signal, is converted by the inverter 414 into a "0" signal and therefore locks out the start switch 417 by the AND-gate 415, since one of the inputs of this AND-gate therefore lies at "0." The operator of the machine must then attend to whatever the response to the condition is, for example, removing the bad workpiece from the production line. Then the reset switch 419 is actuated to feed a "0" pulse through the diodes 420, 421 and 422 to the reset inputs of the multivibrators 401, 403 and 405, respectively. In addition this pulse is fed via a diode 430 to a reset input 242 of the threshold devices 229, 230 and 231 of FIG. 2. This causes the error signal to disappear from the input 431, releasing the relays 412 and 413, and unblocking the AND-gate 415. In addition the multivibrators 401, 403 and 405 are reset in their stable state. The device is then ready to perform another test.

During the integration time established by the time constant of the second monostable multivibrator 403, in accordance with which the condenser of the integrator 215 is charged, the high-voltage might vary or the arc might weaken so that insufficient light is picked up by the respective photocell 212 or insufficient energy is provided to charge the capacitor of the integrator 215 for a significant enough charge to measure. Thus the device will give a false reading if the integrate cycle is stopped before the integrators can build up enough charge to give meaningful results. To this end the switch 424 can be closed and the input at resistor 429 connected to an ouput 243 (FIG. 2) on which lies the voltage of the charging condenser. The potentiometer 428 is adjusted so that the integrator 403 is only reset when sufficient current is present in the basis-metal integrator 215 to give a meaningful readout. For such operation the time constant of integrate multivibrator is adjusted to be longer than could possibly be necessary to obtain a usable result.

Actuation of the reset switch 419 at any time during operation of the device will reset the multivibrators 401, 402 and 405 and allow the device to make another test, even if a test is partially completed. Such actuation of this reset switch 419 also feeds a "0" into the input of NAND-gate 418' and, therefore, causes the flip-flop 418/418' to have no output on its side connected to the one input of the NOR-gate 423. In this condition actuation of the profil switch 424', which is not of the momentary-contact type, feeds a "0" to the other input of the NOR-gate 423, causing its output to be a "1," which locks the NOR-gates 406, 407, and 409 on to close the relays 410, 411 and 413, resepectively.

In this condition the switch 5 will be closed so that an arc will be passed from the counter electrode to the workpiece, assuming the workpiece is in good conductive contact with the holder electrode. Furthermore, as shown in FIG. 3, the pole 301 of the relay 411 will feed the output of the respective photocell through the resistor 302 to the pole 307 of the relay 412. Since this relay 412 is not electrified, however, the resistor will be connected across the charging capacitor 305. Actuation of the relay 413 will cause the amplifier 312 to pick up the output of the photocell through input 300 continuously. Thus no integration takes place, the photocell being hooked directly into the arrangement and the capacitors 303 and 305 merely acting as series-connected smoothing capacitors.

For calibrating with a known testpiece all threshold potentiometers 226, 227 and 228 will be set to minimum threshold, therefore sparking of the testpiece will cause generally an error signal of speaker 238. By setting the switch 239 to each amplifier 220–222 subsequently and setting the potentiometers 223–225 to disappearing voltage of the voltmeter 240 the error signal will be cleared.

Then the potentiometers 229–231 will be adjusted for deviations of contents exceeding the given range.

With such an adjustment all workpieces within the given range of composition can be tested without generation of an error signal.

It will be understood that each of the elements described above, or two or more together, may also find a useful application in other types of circuits differing from the types described above.

While the invention has been illustrated and described as embodied in an alloy-testing system, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A system for testing an alloy workpiece formed of a basis metal and a plurality of alloying elements, said system comprising:
   power-supply means including
      a contact electrode adapted to engage said workpiece,
      a counter electrode adapted to be spaced by a gap from said workpiece, and
      an arc switch operable for passing a unipolar electrical pulse across said gap to form a spark;
   a tester including
      means for diffracting the light of said spark into a spectrum having lines corresponding to said basis metal and to said alloying elements and for converting said lines into respective electrical signals having respective levels corresponding to the intensities of the respective lines,
      means including an integrate switch operable for integrating said electrical signals, and
      means including an evaluate switch operable for reading the integrated signals and for generating an error signal when any of said integrated signals varies from a predetermined range; and
   a control circuit including
      first timer means connected to said arc switch for operating same for a predetermind first period and thereby passing said pulse across said gap during said first period, second time means connected to said arc and integrate switches for operating same for a predetermined second period commencing at the end of said first period to continue passing said pulse and to integrate said electrical signals during said second period, and third timer means unconnected to said arc switch but connected to said evaluate switch for operating said evaluate switch for a predetermined third period commencing at the end of said second period for terminating passage of said pulse across said gap and reading said integrated signals during said third period.

2. The system defined in claim 1, further comprising means for maintaining operation of said evaluate switch on generation of an error signal.

3. The system defined in claim 1, wherein said means for diffracting includes a receive switch which must be operated for conversion of said lines into electrical signals, said system further comprising profiling means connected to said arc, receives, and evaluate switches for operating same in a profiling mode.

4. A method of testing the composition of a workpiece comprising the steps of:
positioning said workpiece in contact with a contact electrode and spaced by a gap from a counter electrode;
passing a unipolar electrical pulse across said gap during a first predetermined period;
thereafter during a second time period commencing at the end of said first period diffracting the light of the spark formed by said pulse into a spectrum having lines corresponding to a plurality of respective components of said workpiece, forming a plurality of respective electrical signals each having a respective signal level corresponding to the intensity of the respective line, integrating said electrical signals, and continuing to pass said pulse across said gap;
ceasing to pass said pulse at the end of said second time period; and
thereafter during a third time period commencing at the end of said second time period comparing the integrated signals with respective reference signals and generating an error signal on any of said integrated signals varying from the respective reference signal by more than a predetermined amount.

5. In combination with a spark-discharge apparatus having
a discharge switch operable to pass a unipolar pulse between a workpiece and an electrode, and
a start switch operable to fire said pulse across said gap, and with a testing apparatus in turn having
means including a charging switch operable for charging at least one capacitor with at least one respective electrical signal corresponding to at least one respective line of a diffraction spectrum produced from the spark created by said pulse,
means including an integrating switch for reading the charge of said capacitor into an evaluating circuit,
means including an evaluating switch for measuring said charge and thereby determining the composition of said workpiece, and
means for forming at an output of said testing apparatus an error signal when a workpiece being tested has a composition varying from a predetermined reference composition, a control circuit comprising:

a first monostable multivibrator having an input and an output;
a first NOR-gate having an output connected to said discharge switch for operating same and at least three inputs one of which is connected to said output of said first multivibrator;
a first inverter having one side connected to one side of said first multivibrator;
a second monostable multivibrator having an input connected to the other side of said first inverter and an output connected to another input of said first NOR-gate;
a second NOR-gate having an input connected to said output of said second multivibrator and an output connected to said charging switch;
a second inverter having one side connected to said output of said second multivibrator
a third monostable multivibrator having an input connected to the other side of said second inverter and an output;
a third NOR-gate having an input connected to said output of said second multivibrator, another input connected to said output of said third multivibrator, and an output connected to said integrating switch;
a start switch linked to the start switch of said discharge apparatus;
a third inverter having one side connected to said start switch of said control circuit;
an AND-gate having one input connected to the other side of said third inverter and an output connected to an input of said first multivibrator;
a fourth inverter having one side connected to said means for forming so as to receive said error signal therefrom and another side connected to the other input of said AND-gate; and
a fourth NOR-gate having an input connected to an output of said third multivibrator and an output connected to said evaluating switch.

6. The improvement defined in claim 5, wherein both said third NOR-gate and said fourth NOR-gate have each another input connected to said one side of said fourth inverter.

7. The improvement defined in claim 5, wherein said first, second and third multivibrators have each a reset connection, said circuit further comprising diodes connected to said reset connections.

8. The improvement defined in claim 7, wherein said testing apparatus includes means for generating a voltage proportional to the charge in said capacitor, said circuit further comprising means for feeding said voltage via another diode to reset said second multivibrator when said charge in said capacitor attains a predetermined level.

9. A system for testing a workpiece formed of a plurality of components, said system comprising:
power-supply means including
a contact electrode adapted to engage said workpiece,
a counter electrode adapted to be spaced by a gap from said workpiece, and
circuitry including an arc switch operable for passing a unipolar electrical pulse across said gap to form a spark;
a tester including means for spectrographically analyzing said spark; and
a control circuit including safety means connected to said arc switch and including a terminal connectable to said workpiece for detecting a closed circuit between said contact electrode and said workpiece and only permitting operation of said arc switch for passing said pulse across said gap when such closed circuit is detected; and timer means connected to said arc switch and to said tester for first passing a pulse across said gap without operation of said tester, whereby foreign matter is burnt off said workpiece at said gap, and for thereafter continuing to pass a pulse while operating said tester to analyze said workpiece.

10. The system defined in claim 9 wherein said means for analyzing includes:

means for diffracting the light of said spark into a spectrum having lines corresponding to said components and for converting said lines into respective electrical signals having respective levels corresponding to the intensities of the respective lines;

means including an integrate switch operable for integrating said electrical signals; and means including an evaluate switch operable for reading the integrated signals and for generating an error signal when any of said integrated signals varies from a predetermined range, said timer means including first timer means connected to said arc switch for operating same for a predetermined first period and thereby passing said pulse across said gap during said first period;

second timer means connected to said arc and integrate switches for operating same for a predetermined second period commencing at the end of said first period to continue passing said pulse and to integrate said electrical signals during said second period; and third timer means unconnected to said arc switch but connected to said evaluate switch for operating same for a predetermined third period commencing at the end of said second period for terminating passage of said pulse across said gap and reading said integrated signals during said third period.

11. The system defined in claim 9 wherein said components include a basis metal and a plurality of alloying elements, said tester including means for evaluating each of said integrated electrical signals corresponding to respective alloying elements with respect to the integrated electrical signal corresponding to the basis metal.

12. The system defined in claim 9 wherein said control circuit includes a start switch in series with said arc switch, whereby said pulse can only pass across said gap when said arc and start switches are both closed.

* * * * *